(12) United States Patent
Inanaga

(10) Patent No.: US 6,391,926 B2
(45) Date of Patent: May 21, 2002

(54) OPTICALLY ACTIVE PHOSPHATE DERIVATIVE

(75) Inventor: Junji Inanaga, Fukuoka (JP)

(73) Assignee: Tosoh Corporation, Yamaguchi-ken (JP)

( * ) Notice: Subject to any disclaimer, the term of this patent is extended or adjusted under 35 U.S.C. 154(b) by 0 days.

(21) Appl. No.: 09/801,041

(22) Filed: Mar. 8, 2001

(30) Foreign Application Priority Data

Mar. 13, 2000 (JP) .................................. 2000-073997

(51) Int. Cl.$^7$ .................... A61K 31/05; C07D 315/00; C07D 309/00; C07F 9/02
(52) U.S. Cl. .................... 514/732; 549/416; 549/356; 558/83; 558/73
(58) Field of Search .................... 514/732; 549/416; 558/83

(56) References Cited

U.S. PATENT DOCUMENTS

| | | | | |
|---|---|---|---|---|
| 3,848,030 A | | 11/1974 | Vitterbo et al. ............. | 260/936 |
| 5,395,962 A | * | 3/1995 | Kawashima ................ | 562/401 |
| 5,510,520 A | * | 4/1996 | Kawashima ................ | 562/401 |
| 6,274,745 B1 | * | 8/2001 | Inanaga et al. ............. | 549/416 |

FOREIGN PATENT DOCUMENTS

EP    1 038 877    9/2000

OTHER PUBLICATIONS

Toda et al Chemistry Letters vol. 1988, pp 131–134, Xp001005242 "New Chiral Shift Reagents etc."

DD 235 251 A (ADW DDR) Apr. 1986 —Abstract.

* cited by examiner

*Primary Examiner*—Zohreh Fay
*Assistant Examiner*—Brian-Yong S. Kwon
(74) *Attorney, Agent, or Firm*—Nixon & Vanderhye

(57) ABSTRACT

An optically active binaphthol derivative of the following formula (1) or (2), an optically active phosphate derivative of the following formula (3) or, (4), processes for their production, and an asymmetry identifying agent comprising the derivative of the formula (3) or (4):

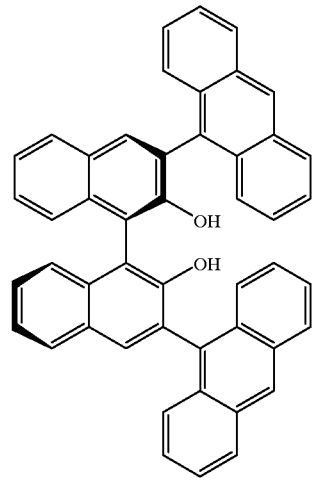

(1)

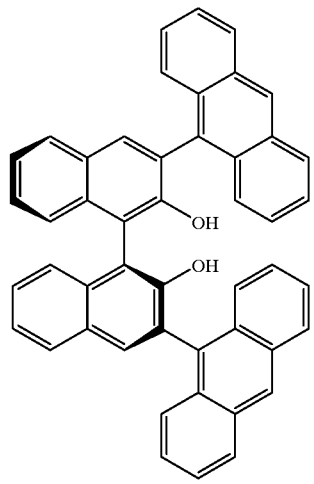

(2)

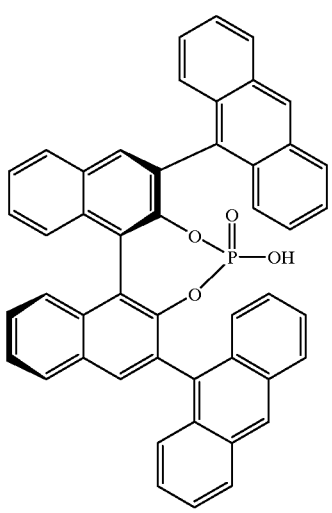

(3)

5 Claims, No Drawings

OPTICALLY ACTIVE PHOSPHATE DERIVATIVE

The present invention relates to an optically active binaphthol derivative and an optically active phosphate derivative, as well as their uses. The optically active binaphthol derivative and the optically active phosphate derivative of the present invention are expected to be useful, for example, as intermediates for the preparation of catalysts for various asymmetric syntheses, and the optically active phosphate derivative of the present invention is, by itself, a useful compound having a high asymmetry-identifying ability.

The optically active binaphthol derivative of the present invention and the optically active phosphate derivative derived therefrom, have not heretofore been known, and they are novel compounds.

As an asymmetry-identifying agent, a complex having europium as the center metal, such as Eu-DPM, Eu-PTA, Eu(hfc) or Eu(Tfc), or (R)-(+)-2-methoxy-2-(trifluoromethyl) phenyl acetic acid, is, for example, commercially available.

Further, it is known that 1,1'-binaphthyl-2,2'-diol which is useful as a catalyst element for asymmetric syntheses is useful also as an optical resolution agent (Toda, F., et, al., Chem. Lett., 131(1988), etc.). Further, as an asymmetry-identifying element, 3,3'-(3,5-diphenylphenyl)-1,1'-binaphthyl-2,2'-diyl phosphoric acid is known (76th annual spring meeting of Chemical Society of Japan, 1999, 3C1 05).

The conventional agents employing metal complexes of e.g. europium, which are commercially available, may react depending upon the compounds subjected to asymmetry-identification, and their application range is limited. Further, (R)-(+)-2-methoxy-2-(trifluoromethyl) phenyl acetic acid or the like has hydrogen bonded to sp3 carbon in the nuclear magnetic resonance spectrum analysis (hereinafter referred to simply as NMR), whereby depending upon the type of the compound subjected to asymmetry-identification, the chemical shift is likely to be overlapped so that the determination can not be made.

On the other hand, 1,1'-binaphthyl-2,2'-diol is an excellent agent having a relatively low reactivity with a compound subjected to asymmetry-identification, but its interaction with the compound subjected to asymmetry-identification is low, whereby it is required to be used in a large amount, and its asymmetry-identifying ability is not fully satisfactory.

Further, 3,3,'-(3,5-diphenylphenyl)-1,1'-binaphthyl- 2,2'-diyl phosphoric acid shows good performance as an asymmetry-identifying agent, but its ability is incomplete, and it has been desired to develop an agent having a still higher performance.

In order to solve the above problems, the present inventors have conducted an extensive study with an aim to develop a compound having a higher asymmetry-identifying ability and as a result, have found a novel binaphthol derivative as an intermediate and a novel optically active phosphate derivative as an asymmetry-identifying agent. The present invention has been accomplished on the basis of this discovery.

Namely, the present invention provides:

an optically active binaphthol derivative of the following formula (1) or (2):

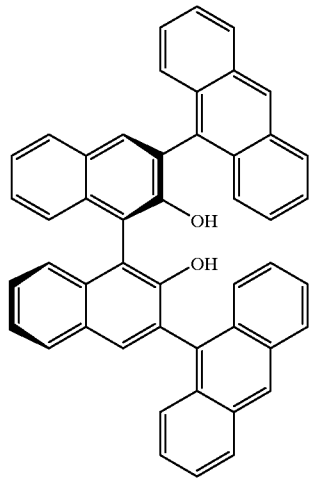

(1)

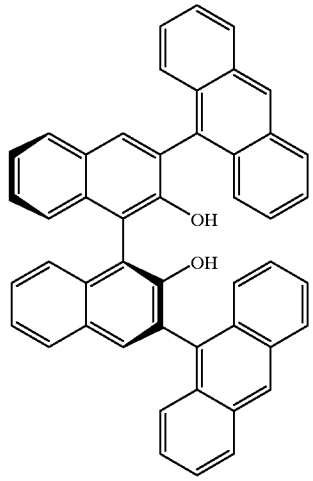

(2)

a process for producing the optically active binaphthol derivative, which comprises reacting 9-anthryl boric acid with (R) or (S)-3,3'-diiodo-1,1'-binaphthyl-2,2'-diyl bis(methoxy methyl ether), followed by hydrolysis;

an optically active phosphate derivative of the following formula (3) or (4):

(3)

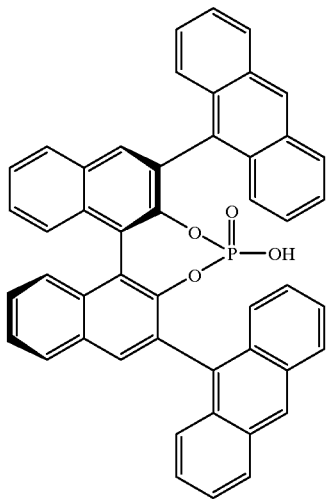

(4)

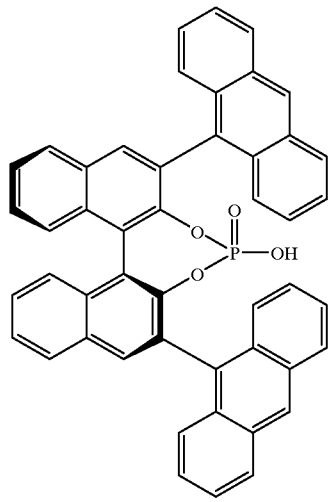

a process for producing the phosphate derivative, which comprises reacting an optically active binaphthol derivative of the above formula (1) or (2) with phosphorus oxychloride, followed by hydrolysis; and an asymmetry-identifying agent comprising a phosphate derivative of the above formula (3) or (4).

Now, the present invention will be described in detail with reference to the preferred embodiments.

The binaphthol derivative of the above formula (1) or (2) of the present invention can be prepared by reacting 9-anthryl boric acid obtainable by a method known in literature, with 3,3'-diiodo-1,1'-binaphthyl-2,2'-diyl bis (methoxymethyl)ether obtainable likewise by a method known in literature using commercially available optically active (R) or (S) 1,1'-binaphthyl-2,2'-diol as the starting material, followed by hydrolysis to remove any protecting group. The obtained binaphthol derivative of the above formula (1) or (2) can be converted to the optically active phosphate derivative of the above formula (3) or (4) by reacting it with phosphorus oxychloride, followed by hydrolysis.

The conditions for producing the compound of the above formula (1) or (2) of the present invention are not particularly limited. For example, in a 1,2-dimethoxyethane solvent, in the presence of tetrakis(triphenylphosphine) palladium(O) as a catalyst and barium hydroxide as a base, (R) or (S) 3,3'-diiodo-1,1'-binaphthyl-2,2'-diyl bis (methoxymethyl)ether and 9-anthryl boric acid may be reacted for about 24 hours under a heating condition to obtain 3,3'-bis(9-anthryl)-1,1'-binaphthyl-2,2'-diyl bis (methoxymethyl)ether, which is then reacted for about one day under a heated condition in a toluene/methanol/hydrochloric acid aqueous solution, to obtain the desired product.

The conditions for producing the phosphate derivative of the above formula (3) or (4) of the present invention are not particularly limited. For example, the binaphthol derivative of the above formula (1) or (2) and phosphorus oxychloride may be reacted in a dichloromethane solvent in the presence of triethylamine at room temperature for about 12 hours, and then reacted for about 12 hours in the presence of sodium carbonate in a tetrahydrofuran (hereinafter referred to as THF)/water solvent under a heated condition, and further heated for about 12 hours in an aqueous hydrochloric acid solution, to obtain the desired product.

In the processes of the present invention, there is no particular restriction as to the proportions of the reagents, the amount of the solvent, the temperature, the time, etc.

With respect to their applications, the compounds of the above formulae (1) to (4) of the present invention can be used as asymmetric elements for catalysts for asymmetric syntheses, optical resolution agents, packing materials for optically active columns and asymmetry-identifying agents in NMR measurements.

Now, an application as an asymmetry-identifying agent in NMR measurement will be described.

The optically active phosphate derivative of the present invention has no sp3 carbon, whereby its chemical shift will not overlap with a compound subjected to asymmetry-identification in the NMR measurement.

As a specific method of use of the phosphate derivative of the present invention as an asymmetry-identifying agent in NMR measurement, predetermined amounts of the phosphate derivative of the present invention and the compound to be subjected to asymmetry-identification, are mixed and dissolved in a solvent for NMR measurement, such as heavy chloroform or heavy benzene, whereupon the chemical shift is measured by proton NMR or carbon NMR.

Compounds to which the phosphate derivative of the present invention is applicable as an asymmetry-identifying agent, are not particularly limited. However, the phosphate derivative of the present invention shows an asymmetry-identifying ability against alcohols, amines, carboxylic acids and sulfoxides, which have asymmetry.

The amount of the phosphate derivative of the present invention to be used as an asymmetry-identifying agent should theoretically adequately be an equimolar amount to an optical isomer to form coordination, and a high identification ability can in fact be thereby obtainable. However, there may be a case where the identification ability will be further increased by using it in an amount of about 2 mols, as the case requires. Specifically, in a case where asymmetry-identification of a racemic alcohol is carried out, an adequate asymmetry-identifying ability will be obtained by an addition of only 0.5 mol of the phosphate derivative of the present invention. Usually, when a racemic alcohol is subjected to asymmetry-identification employing (R)-3,3'-bis(9-anthryl)-1,1'-binaphthyl-2,2'-diyl phosphoric acid of the above formula (3), the chemical shift of hydrogen bonded on the carbon atom bonded to the hydroxyl group or on the carbon atom adjacent to the carbon atom bonded to a hydroxyl group, is shifted more towards the high magnetic field side in the S-isomer than in the R-isomer.

The novel optically active binaphthol and optically active phosphate derivative of the present invention are compounds useful as pharmaceuticals or intermediates for their preparation, agricultural chemicals or intermediates for their preparation, functional materials such as electronic materials or intermediates for their preparation, catalysts for asymmetric syntheses, asymmetric elements for the catalysts for asymmetric syntheses, optical resolution agents, optical active column packing materials, and asymmetry-identifying agents in NMR measurements.

Further, when the phosphate derivative of the present invention is used as an asymmetry-identifying agent in NMR measurement, it provides a high asymmetry-identifying ability, whereby a simple and convenient method for measuring the optical purity can be presented.

Now, the present invention will be described in further detail with reference to Examples. However, it should be understood that the present invention is by no means restricted to such specific Examples.

Measurement of Optical Rotation SEPA-300, manufactured by HORIBA, was used.
Measurement of Melting Point MP-500D, manufactured by Yanako K.K., was used.
Measurements of $^1$H-NMR and $^{13}$C-NMR JNM-EX400, manufactured by JEOL, was used (400 MHz).
Measurement of HRFABMASS JMS-HX100A, manufactured by JEOL, was used.
Measurement of IR JIR-WINSPEC50, manufactured by JEOL, was used.
Elemental Analysis
Carried out by Central Analysis Center of Kyusyu University.

EXAMPLE 1

Preparation of (R)-3,3'-bis(9-anthryl)-1,1'-binaphthyl-2,2'-diol

Into a 200 ml eggplant-type three necked flask equipped with a reflux condenser, a septum cap and a magnetic stirrer, 134 mg (0.12 mmol) of tetrakis(triphenylphosphine)palladium(O), 2.8 g (12.8 mmol) of 9-anthryl boric acid and 5.5 g (19.0 mmol) of barium hydroxide octahydrate were charged. Then, the interior of the system was flushed with argon, and then a solution prepared by dissolving 3.64 g (5.8 mmol) of (R)-3,3'-diiodo-1,1'-binaphthyl-2,2'-diyl bis(methoxymethyl)ether in 50 ml of 1,2-dimethoxyethane, was injected into the system through the septum by means of a syringe of 50 ml, and 10 ml of water was further added.

The obtained mixture was heated to 80° C. on an oil bath with stirring and reacted at the same temperature for 24 hours.

After completion of the reaction, the mixture was cooled to room temperature and then extracted with ethyl acetate, followed by washing with a saturated sodium chloride aqueous solution, drying over magnesium sulfate, concentration and purification by silica gel column chromatography (hexane/ethyl acetate=20/1), to obtain 2.97 g of (R)-3,3'-bis(9-anthryl)-1,1'-binaphthyl-2,2'-diyl bis(methoxymethyl) ether, as a slightly yellow solid (yield: 70%).

Analytical Results
Melting point: 263–265° C.
Optical rotation: $[\alpha]_D^{17.7}$ +236.3° (c=1.00 THF)
$^1$H-NMR(CDCl$_3$) δ8.53(s, 2H, aromatic), 8.07–7.88(m, 10H, aromatic), 7.78(d, 2H, J=8.79 Hz, aromatic), 7.64–7.62 (m, 2H, aromatic), 7.50–7.37(m, 10H, aromatic), 7.22–7.19 (m, 2H, aromatic), 4.25(dd, 4H, J=5.38, 18.58 Hz, OCH$_2$O), 1.86(s, 6H, OCH$_3$)
$^{13}$C-NMR(CDCl$_3$) δ152.58, 134.11, 133.35, 133.03, 132.38, 131.35, 131.28, 130.79, 130.71, 130.68, 128.43, 128.19, 128.01, 127.02, 126.73, 126.60, 126.36, 125.81, 125.63, 125.35, 125.15, 125.12, 98.21, 55.37
IR(KBr, ν cm$^{-1}$)3051, 2995, 2964, 2823, 1622, 1492, 1444, 1429, 1389, 1346, 1320, 1232, 1203, 1160, 1094, 1071, 1032, 976, 921, 890, 844, 791, 739, 618, 538, 511, 476, 418
HRFABMASS m/z Measured value 726.2770(M)$^+$,
(Measured value C$_{52}$H$_{38}$O$_4$: 726.2770)

Into a 50 ml eggplant-type flask equipped with a reflux condenser and a magnetic stirrer, 558 mg (0.77 mmol) of (R)-3,3'-bis(9-anthryl)-1,1'-binaphthyl-2,2'-diyl bis(methoxymethyl)ether, 6 ml of toluene and 3 ml of methanol were charged and dissolved. Then, five drops of 12N hydrochloric acid were added thereto, followed by heating to 80° C., and a reaction was carried out for 24 hours.

After completion of the reaction, the product was extracted with ethyl ether, washed with a saturated sodium chloride aqueous solution and dried over magnesium sulfate, followed by purification by silica gel column chromatography (hexane/ethyl acetate=20/1) to obtain 450 mg of the desired product (R)-3,3'-bis(9-anthryl)-1,1'-binaphthyl-2,2'-diol as a while solid of monohydrate (yield: 89%).

Analytical Results
Melting point: 300–302° C.
Optical rotation: $[\alpha]_D^{17.4}$ +198.65° (c=1.00, THF)
$^1$H-NMR(CDCl$_3$) δ8.58(s, 2H, aromatic), 8.11–8.04(m, 4H, aromatic), 8.02(s, 2H, aromatic), 7.94–7.23(m, 20H, aromatic), 5.08(s, 2H, —OH)
$^{13}$C-NMR(CDCl$_3$) δ150.98, 133.88, 133.03, 131.46, 131.39, 130.80, 130.73, 129.24, 128.66, 128.52, 128.44, 127.75, 127.37, 127.11, 126.14, 125.31, 124.82, 124.24, 114.49
IR(KBr, ν cm$^{-1}$)3533, 3051, 2924, 2854, 1929, 1803, 1715, 1624, 1497, 1442, 1405, 1383, 1354, 1257, 1208, 1147, 1093, 1013, 950, 889, 845, 795, 738, 614, 541, 516, 468
HRFABMASS m/z Measured value 638.2200(M)$^+$,
(Calculated value C$_{48}$H$_{30}$O$_2$:638.2246)
Elemental analysis (%) Measured values C, 87.92;H, 4.98
(Calculated values C$_{48}$H$_{32}$O$_3$:C, 87.78; H, 4.91)

EXAMPLE 2

Preparation of (R)-3,3'-bis(9-anthryl)-1,1'-binaphthyl-2,2'-diyl phosphoric acid Into a 12 ml round flask containing a magnetic stirrer, 76.6 mg (0.12 mmol) of (R)-3,3'-bis(9-anthryl)-1,1'-binaphthyl-2,2'-diol, 1 ml of dichloromethane and 0.18 ml (1.96 mmol) of phosphorus oxychloride were charged in an argon stream and cooled to 0° C. under stirring. Then, 0.41 ml (2.94 mmol) of triethylamine was dropwise added thereto. After completion of the dropwise addition, the mixture was returned to room temperature and reacted for 12 hours.

After completion of the reaction, water was added, and the product was extracted with dichloromethane, washed with water and dried over magnesium sulfate, and then it was concentrated to obtain crude (R)-3,3'-bis(9-anthryl)-1,1'-binaphthyl-2,2'-diyl phosphoric acid chloride, which was used for the next reaction without purification.

Into a 10 ml round flask containing a magnetic stirrer, the entire amount of the obtained crude (R)-3,3'-bis(9-anthryl)-1,1'-binaphthyl-2,2'-diyl phosphoric acid chloride, 8 ml of THF and 1 ml of a 2% sodium carbonate aqueous solution were charged, heated with stirring and reacted at 700° C. for 12 hours. After completion of the reaction, the reaction product was concentrated under reduced pressure, and then, the obtained residue was washed with a 2% sodium carbonate aqueous solution.

The obtained residue was further dissolved in 8 ml of water and 6 ml of 6N hydrochloric acid and reacted at 800° C. for 12 hours with stirring. Then, the obtained reaction mixture was cooled to 0° C., and the precipitate was collected by filtration and dried at 100° C. under reduced pressure to obtain 58.8 mg of the desired product (R)-3,3'-bis(9-anthryl)-1,1'-binaphthyl-2,2'-diyl phosphoric acid as a yellow solid (yield:70%).

Analytical Results

Optical rotation: $[\alpha]_D^{16.6}$ −12.10° (c=1.00, EtOH)

$^1$H-NMR(CDCl$_3$) δ8.19(s, 2H, aromatic), 8.00(s, 2H, aromatic), 7.92(dd, 4H, J=8.30, 48.34 Hz, aromatic), 7.71–7.11 (m, 20H, aromatic)

$^{13}$C-NMR(CDCl$_3$) δ146.48, 146.39, 133.80, 132.63, 131.33, 131.17, 130.88, 130.80, 130.71, 130.64, 130.24, 128.46, 127.82, 127.42, 127.33, 126.87, 126.09, 126.01, 125.79, 124.95, 124.79, 122.32

HRFABMASS m/z Measured value 701.1884(M+H)$^+$, (Calculated value C$_{48}$H$_{30}$ O$_4$P:701.1882)

EXAMPLES 3 to 7

Into a NMR measurement tube, from 2 to 5 mg of the compound identified in Table 1 and 0.6 ml of heavy chloroform were introduced, and 0.5 mol or 1.0 mol, per mol of the compound identified in Table 1, of (R)-3,3'-bis(9-anthryl)-1,1'-binaphthyl-2,2'-diyl phosphoric acid prepared in Example 2, was added thereto, and the measurement was carried out. The results are shown in Table 1.

Comparative Examples 1 and 2

The measurement was carried out under the condition shown in Table 1 by changing (R)-3,3'-bis(9-anthryl)-1,1'-binaphthyl-2,2'-diyl phosphoric acid to 1,1'-binaphthyl-2,2'-diol. The results are shown in Table 1.

COMPARATIVE EXAMPLES 3 and 4

The measurement was carried out under the condition shown in Table 1 by changing (R)-3,3'-bis(9-anthryl)-1,1'-binaphthyl-2,2'-diyl phosphoric acid to (R)-3,3'-bis(3,5-diphenylphenyl)-1,1'-binaphthyl-2,2'-diyl phosphoric acid. The results are shown in Table 1.

TABLE 1

| Example No. | Compound[1] | | Δ δ 1[2] (0.5 mol added) | Δ δ 1[3] (1.0 mol added) |
|---|---|---|---|---|
| Ex. 3 | Compound (1) | Ha | 0.049 | 0.089 |
|  |  | Me | 0.049 | 0.089 |
| Ex. 4 | Compound (2) | Ha | 0.034 | 0.073 |
|  |  | Me | 0.023 | 0.046 |
| Ex. 5 | Compound (3) | Ha | 0.15 | 0.28 |
|  |  | Me | 0.015 | 0.30 |
| Ex. 6 | Compound (4) | Ha | 0.10 | 0.19 |
|  |  | Me | 0.13 | —[4] |
| Ex. 7 | Compound (5) | Me | 0.039 | 0.077 |
| Comp. Ex. 1 | Compound (1) | Ha | | 0.040[5] |
|  |  | Me | | 0.040 |
| Comp. Ex. 2 | Compound (5) | Me | | 0.013 |
| Comp. Ex. 3 | Compound (1) | Ha | 0.039 | 0.082 |
|  |  | Me | —[6] | 0.031 |
| Comp. Ex. 4 | Compound (4) | Ha | —[6] | —[6] |
|  |  | Me | —[6] | 0.010 |

[1]Compound (1): (±)-1-phenethyl alcohol: PhCHa(OH)Me
Compound (2): (±)-1-phenyl-1-methoxy acetic acid; PhCHa(OMe)COOH
Compound (3): (±)-2-octanol: C$_6$H$_{13}$CHa(OH)Me
Compound (4): (±)-2-butanol: C$_2$H$_5$CHa(OH)Me
Compound (5): (±)-phenylmethyl sulfoxide; PhS(O)Me
[2]Chemical shift of the peak separated when 0.5 mol of the agent was added (ppm).
[3]Chemical shift of the peak separated when 1.0 mol of the agent was added (ppm).
[4]The peak was separated but overlapped with other peak, whereby no calculation was possible.
[5]2.0 mol of the agent was added.
[6]No peak was separated.

The entire disclosure of Japanese Patent Application No. 2000-073997 filed on Mar. 13, 2000 including specification, claims, drawings and summary are incorporated herein by reference in its entirety.

What is claimed is:

1. An optically active binaphthol derivative of the following formula (1) or (2):

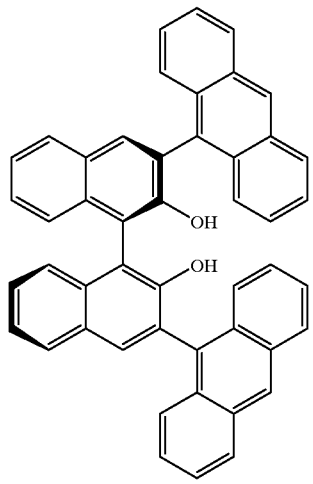
(1)

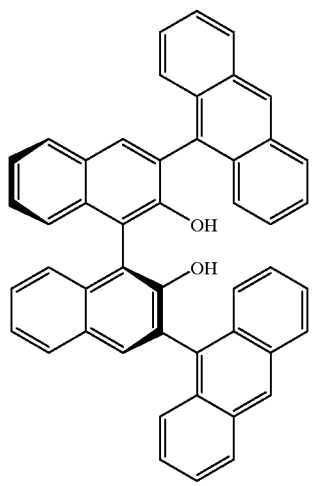
(2)

2. A process for producing the optically active binaphthol derivative as defined in claim 1, which comprises reacting 9-anthryl boric acid with (R) or (S)-3,3'-diiodo-1,1'-binaphthyl-2,2'-diyl bis(methoxy methyl ether), followed by hydrolysis.

3. An optically active phosphate derivative of the following formula (3) or (4):

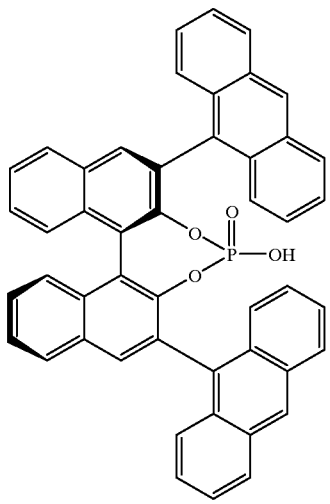
(3)

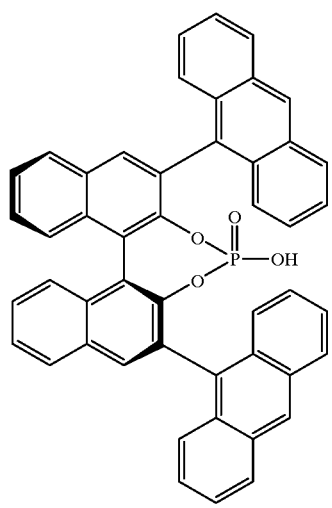
(4)

4. A process for producing the phosphate derivative as defined in claim 3, which comprises reacting an optically active binaphthol derivative of the following formula (1) or (2):

(1)
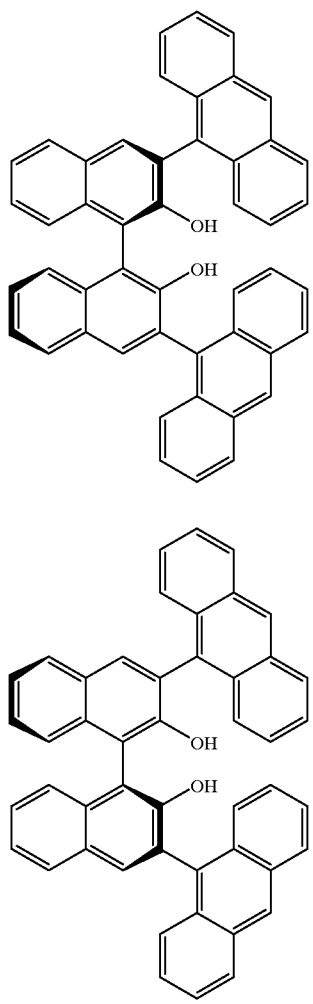
(2)
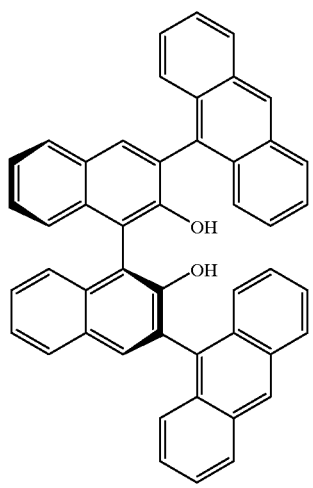
(3)
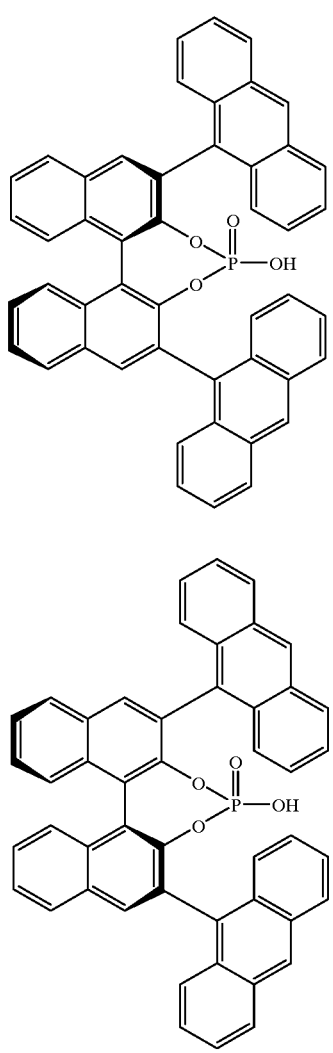
(4)
with phosphorus oxychloride, followed by hydrolysis.
5. An asymmetry-identifying agent comprising a phosphate derivative of the following formula (3) or (4):
* * * * *